United States Patent [19]
Swarup et al.

[11] Patent Number: 5,296,541
[45] Date of Patent: Mar. 22, 1994

[54] POLYAZETIDINOL CONTAINING MATERIALS

[75] Inventors: Shanti Swarup; Gregory J. McCollum, both of Gibsonia, Pa.

[73] Assignee: PPG Industries, Inc., Pittsburgh, Pa.

[21] Appl. No.: 109,895

[22] Filed: Aug. 23, 1993

Related U.S. Application Data

[62] Division of Ser. No. 814,655, Dec. 30, 1991.
[51] Int. Cl.$^5$ ................................ C08F 8/30
[52] U.S. Cl. .................... 524/556; 524/558; 525/328.8; 525/329.4; 525/329.9; 525/375; 525/437; 525/453; 525/523
[58] Field of Search ............ 524/556, 558; 525/328.8, 329.4, 329.9, 375, 437, 453, 523

[56] References Cited

U.S. PATENT DOCUMENTS

| | | |
|---|---|---|
| 3,290,416 | 12/1966 | Christenson et al. |
| 3,290,417 | 12/1966 | Christenson et al. |
| 3,386,939 | 6/1968 | Mesec |
| 3,634,399 | 1/1972 | Coscia et al. |
| 3,705,076 | 12/1972 | Usala |
| 4,189,468 | 2/1980 | Vanlerberghe et al. |
| 4,576,980 | 3/1986 | Dai et al. |
| 4,612,098 | 9/1986 | Dai et al. |
| 4,735,984 | 4/1988 | Gouji et al. |

FOREIGN PATENT DOCUMENTS

507407 11/1992 European Pat. Off.

OTHER PUBLICATIONS

"A General Method for the Synthesis of Substituted Azetidines", S. S. Chatterjee and A. Shoeb, Synthesis 3, pp. 153–154, 1973.

"Synthesis and Cyclodimerization of Stable 1-t-alkylamino-2,3-epoxypropanes; Related Sterically Promoted Eight-Membered Ring Closures," V. R. Gaertner, Tetrahedron Letters No. 3, pp. 141–146, 1964, Pergamon Press.

"Cyclization of 1-alkylamino-3-halo-2-alkanols to 1-alkyl-3-azetidinols," V. R. Gaertner, Tetrahedron Letters No. 39, pp. 4691–4694, 1966, Pergamon Press Ltd.

"Polymerization via Betaine. V. Alternating Copolymerization of 1,3,3-Trimethylazetidine with Acrylic Acid. A Novel Method for the Preparation of Amine-Ester Type Polymer", Takeo Saegusa, Yoshiharu Kimura, Satoru Sawada and Shiro Kobayashi, Macromolecules, Communications to the Editor, vol. 7, No. 6, pp. 956–958, 1974.

"Reactive Polymers Containing Pendant Azetidine or Azetidinium Functions, 1", Yvan Bogaert, Eric Goethals and Etienne Schacht, Makromol. Chem. 182, pp. 2687–2693, 1981.

"Polymers Derives from N-alkyl Azetidinols", Eric J. Goethals, Jianing Huang and Dirk Mestach, Polymer Preprint, vol. 31, pp. 57–58, 1990.

"Studies on Azetidine Derivatives. I. Synthesis of 3-Substituted Azetidine Derivatives", Tetsuya Okutani, Tatsuhiko Kaneko and Katsutada Masuda, Chem. Pharm. Bull., vol. 22, No. 7, pp. 1490–1497, (1974).

"Ketenes. XIV. Adducts of Dimethylketene with C=N Compounds", James C. Martin, Kent C. Brannock, Robert D. Burpitt, P. Glenn Gott and V. A. Hoyle, Jr., J. Org. Chem., vol. 36, No. 16, pp. 2211–2215, 1971.

"New investigations of the reaction of epichlorohydrin with hindered amines: X-ray and NMR analyses", Michel Laguerre, Chantel Boyer, Jean-Michel Leger and Alain Carpy, Can. J. Chem., vol. 67, pp. 1514–1522, 1989.

"Preparation of 3-Azetidinols with Non-Bulky 1-Alkyl Substituents", Robert H. Higgins, Quentin L. Eaton, Leroy Worth, Jr. and Myra V. Peterson, J. Heterocyclic Chem., vol. 24, pp. 255–259, 1987.

"Cationic Polymerization of Cyclic Amines, 7 Ethyl 3-Azethdinylpropionate", Jan Lukaszczyk, Etienne H. Schacht and Eric J. Goethals, Makromol. Chem., Rapid Commun. 1, pp. 79–84, 1980.

"Cyclization of 1-Alkylamino-3-halo-2-alkanols to 1-Alkyl-3-azetidinols", V. R. Gaertner, J. Organic, vol. 32, pp. 2972–2976, 1967.

*Primary Examiner*—Bernard Lipman
*Attorney, Agent, or Firm*—Linda Pingitore

[57] ABSTRACT

A reaction product is prepared from a polycarboxylic acid group containing polymeric material and a polyazetidinol of a specific structural formula. The polyazetidinol can also be formulated into curable compositions both as film forming vehicle or alternatively as an additive to improve mar and humidity resistance.

15 Claims, No Drawings

POLYAZETIDINOL CONTAINING MATERIALS

This is a divisional of application Ser. No. 07/814,655, filed Dec. 30, 1991.

CROSS REFERENCE TO RELATED APPLICATIONS

The present application is related to U.S. patent application Ser. No. 07/814,655 filed on Dec. 30, 1991, entitled Azetidinol Reaction Products.

BACKGROUND OF THE INVENTION

The present invention relates to azetidinol containing materials having at least two azetidinol moieties per molecule and reaction products and curable compositions prepared therewith.

In U.S. patent application Ser. No. 07/814,655, filed Dec. 30, 1991, entitled Azetidinol Reaction Products, azetidinol containing materials having one azetidinol moiety per molecule are disclosed as grind vehicles for the preparation of a variety of pigmented coating compositions and also as modifiers for acrylic polymers and oligomers as well as other polymers and oligomers without the handling hazards associated with certain other small nitrogen ring containing materials. These modified materials, however, are non thermoset materials which require a crosslinking agent to produce a cured product. As a result, the curing process releases undesirable volatile byproducts of a curing reaction with aminoplast or polyisocyanate crosslinkers.

Although quite advantageous, the modified azetidinols described above are limited in their applicability since they are incapable of self-crosslinking or reacting with other oligomers to form cured films without externally added crosslinking agents.

The preparation of azetidinols with such properties would be desirable and advantageous.

SUMMARY OF THE INVENTION

In accordance with the present invention there is provided a reaction product of a polycarboxylic acid group containing polymeric material and a polyazetidinol of a specific structural formula. Also provided are curable compositions containing the aforesaid polyazetidinol as a film forming vehicle or alternatively as an additive for improving mar and humidity resistance.

DETAILED DESCRIPTION OF THE INVENTION

The claimed organic compounds having at least two azetidinol moieties per molecule, polyazetidinols, are very advantageous not only as self-crosslinkable film forming binders but also as curing agents for other polymers and oligomers as well as additives and modifiers for a variety of solvent and waterborne coatings to improve overall film properties. For example, when used to form a reaction product with an acid functional oligomer or polymer, the reaction product is shelf stable and capable of self-crosslinking to form a film in about 30 minutes at a temperature of from about 180° F. (82° C.) to about 250° F. (121° C.). The polyazetidinols are themselves shelf stable at ambient temperature for a period of several months or at elevated temperatures of about 140° F. (60° C.) for a week or more in either solvent or aqueous medium provided the pH is within the range of from about 6 to 9 under partial neutralization conditions of 5 to 50 percent of amine. The polyazetidinols are capable of forming a film at temperatures of from ambient to about 400° F. (205° C.) for a period of from about 1 week to less than 30 minutes, respectively. The resultant films are clear and solvent resistant as measured by solvent rubs.

In addition to their utility as film formers, the polyazetidinols described above are very advantageous as additives to waterborne, aminoplast curable, coating compositions in order to improve humidity resistance. It is theorized that this is accomplished because the hydroxyl groups of the polyazetidinol material react with and consume any residual carboxyl groups present which contribute to water sensitivity.

The organic compounds of the present invention having at least two azetidinol moieties per molecule can be represented by the following structural formula

In the above formula n is an integer of from 2 to 4 and R is the residue derived from a polyfunctional amine. Examples of residues representative of R include alkylene, arylene, aralkylene, cycloalkylene or heteroatom substituted derivatives thereof. The amine is one of the reactants from which the polyazetidinol is prepared. The preferred amines are relatively hindered primary amines. By "hindered" is meant that the amino group is attached to a carbon that is in the vicinity of a bulky group. The other reactant is an epihalohydrin such as for example epichlorohydrin or epibromohydrin. Examples of polyfunctional amines include bis-4-(aminocyclohexyl) methane which is commercially available from Texaco Chemicals under the trademark PACM ®-20; isophorone diamine; polyoxypropylene diamine which is commercially available from Texaco Chemicals as JEFFAMINE ® D400 and JEFFAMINE ® T403 which is a triamine derived from the reaction product of propylene oxide with a triol.

The polyazetidinols having at least two azetidinol moieties per molecule generally can be prepared by the reaction of the polyfunctional amine with epihalohydrin followed by removal of hydrogen halide. The reaction is preferably conducted in the presence of a polar solvent such as butanol, acetonitrile, ethanol, isopropanol, methanol, dimethylformamine or dimethylsulfoxide.

After the initial mixing, the polyfunctional amine and epihalohydrin are reacted at a temperature and for a period sufficient to form the hydrohalide salt of the polyfunctional azetidinol. Generally the reaction temperature ranges from about 60° C. to about 80° C. and the time of reaction ranges from about 1 to about 6 hours.

Preferably, the hydrochloride salt of the polyazetidinol is converted to the free amine base by neutralization with aqueous sodium hydroxide. The product is then stripped to remove water and the salt removed by filtration to yield a solution of the polyazetidinol.

The polyazetidinols of the present invention are capable of self crosslinking to form a cured film or they can be used to make gelled or ungelled reaction products with a variety of other oligomers and polymers. Also, they can be utilized as additives to waterborne, aminoplast curable coating compositions to improve mar and humidity resistance.

Useful compositions containing the polyazetidinols can be prepared by blending the polyazetidinol with a carboxylic acid group containing polymeric material. For example, when the carboxylic acid group containing polymeric material is an acrylic polymer, the polymer can be prepared by addition of monomer and initiator to a solvent charge under reflux conditions over a period of about 1 to 5 hours. Upon completion of the monomer and initiator feed, the polymer is neutralized with an appropriate base either at ambient temperature or elevated temperature so long as the temperature is below the boiling point of the solvent and the base. Finally, the polyazetidinol is added at ambient temperature to yield the ungelled product. These compositions can then be further used to prepare coating films by curing the material by baking at elevated temperature.

The polyazetidinols can also be utilized as curing agents for a variety of other polymeric materials.

Examples of suitable materials which can be cocured with the polyazetidinols include vinyl addition polymers prepared from the vinyl addition polymerization of vinyl monomers, polyesters, polyethers, polyurethanes and polyamides. A detailed description of all of these materials is not felt to be necessary since one skilled in the art of coatings enjoys extensive knowledge of these materials. If additional information is desired reference is made to Kirk Othmer, Encyclopedia of Polymer Science and Technology, John Wiley and Sons, Inc. Copyright 1964.

A preferred polymeric material is a carboxylic acid functional acrylic polymer which is described in further detail below. The aforesaid acrylic polymer can be prepared by the vinyl addition polymerization of a vinyl monomer component which comprises at least a portion of a carboxyl functional vinyl monomer.

Examples of suitable carboxyl functional vinyl monomers include acrylic acid, methacrylic acid, monoesters of unsaturated dicarboxylic acids such as maleic acid, fumaric acid, and itaconic acid, for example, mono(hydroxyethyl) and mono(hydroxypropyl) esters of maleic acid. The balance of the vinyl monomer component can include a variety of other vinyl monomers which contain polymerizable vinyl unsaturation. For example, hydroxyl functional vinyl monomers such as 2-hydroxyethyl acrylate, 2-hydroxyethyl methacrylate, 2-hydroxypropyl acrylate, 2-hydroxypropyl methacrylate and 2-hydroxybutyl methacrylate. Also useful are acrylamide; N-methylolacrylamide and N-alkoxymethyl acrylamides such as N-ethoxymethyl acrylamide and N-butoxymethylacrylamide; tertiary-butylaminoethyl methacrylate; sulfoethyl methacrylate; and alkyl acrylates and methacrylates which contain from 1 to 18 carbon atoms in the alkyl portion such as methyl (meth)acrylate, ethyl (meth)acrylate, propyl (meth)acrylate, butyl (meth)acrylate, pentyl (meth)acrylate, hexyl (meth)acrylate, heptyl (meth)acrylate, 2-ethylhexyl (meth)acrylate, lauryl (meth)acrylate, stearyl (meth)acrylate, isodecyl (meth)acrylate and isobornyl (meth)acrylate. Also useful are styrene, paramethyl styrene, alpha-methyl styrene, acrylonitrile, methacrylonitrile and vinyl esters such as vinyl acetate or vinyl versatate. Mixtures of the aforesaid monomers can also be utilized. Preferably, the acrylic polymer has a number average molecular weight ranging from about 500 to about 50,000, more preferably about 2000 to about 20,000.

Preparation of the vinyl addition polymer is usually conducted at a temperature within the range of about 25° C. to about 250° C., preferably 85° C. to 160° C. There is generally present a free radical initiator which is selected from a wide variety of materials. Suitable types of materials include peroxides, hydroperoxides and azo initiators. Examples of these types of initiators include di-tertiary butyl peroxide, di-cumyl peroxide; amyl peroxyacetate; cumene hydroperoxide; 2,5-dimethyl-2,5-bis(tertiary butyl peroxy)hexane; hexyne-3-tertiary butyl cumyl peroxide; tertiary amyl peroxide; 2,5-dihydroperoxy 2,5-dimethylhexane; di(n-propyl)-peroxydicarbonate and 2,2'-azobis(2,4-dimethyl-4-methoxyvaleronitrile). Also suitable are Redox initiators such as the combination of hydrogen peroxide and isoascorbic acid. Transition metals such as iron are usually used as coinitiators with a Redox initiator system.

The type and amount of initiator will be selected depending upon the molecular weight desired and/or the final form of the polymeric species, i.e., solvent soluble form or dispersed form in aqueous or non-aqueous media. The amount of initiator can vary widely although usually it is present in an amount ranging from about 0.1 percent to about 80 percent, the percent based on the total weight of the vinyl monomer component. Generally, there can also be present during the vinyl addition polymerization a solvent. Examples of these solvents include ketones such as methyl amyl ketone, aromatic petroleum distillates, esters such as butyl acetate, heptyl acetate and 2-ethylhexyl acetate, and high boiling ester solvents such as those commercially available from Exxon Chemical Corporation under the trademark designations EXTATE 600 and EXTATE 700.

It should be understood that the carboxylic acid functional acrylic polymers may also be prepared by conventional suspension, emulsion and non-aqueous dispersion polymerization techniques.

The polyazetidinols of the present invention form crosslinked films either alone or in the presence of other film forming components. Film formation may be accomplished at room temperature or under baking conditions, as a solvent based or water based system. The cured films are mar resistant.

A curable composition can also be prepared from the polyazetidinols detailed above in conjunction with a base neutralized acid functional waterborne dispersion or solution polymer. This composition can be applied and cures well at a temperature of 200° F. (93° C.) to 300° F. (149° C.) for a period of about 30 minutes. Examples of suitable base neutralized acid functional waterborne solution or dispersion polymers include base neutralized acid functional polyesters, acid functional polyester urethanes, acid functional acrylates and acid functional urethane-acrylates. The preparation of these materials is well understood by those skilled in the art of polymer chemistry. If additional details are desired reference is made to Kirk Othmer, Encyclopedia of Polymer Science and Technology, John Wiley and Sons, Inc. Copyright 1964.

The polyazetidinols of the present invention are also advantageous as additives for aqueous based coating compositions to improve humidity resistance. For example, the polyazetidinols can be combined with a waterborne film forming vehicle and an aminoplast crosslinking agent.

Such curable (crosslinkable) or thermosetting compositions can be formulated as clear coats or optionally they can contain a pigment. The pigments can be any of the conventional types comprising, for example, iron oxides, lead oxides, strontium chromate, carbon black, coal dust, titanium dioxide, talc, barium sulfate, as well as the color pigments such as cadmium yellow, cadmium red, chromium yellow, phthalocyanine blue, toluidine red, and the metallic pigments such as aluminum flake and metal oxide encapsulated mica. When used, the pigment content of the coating composition is expressed as a pigment to resin weight ratio, and is usually within the range of about 0.05 to 3.0:1.

In addition, other optional ingredients such as adjuvant hydroxy-containing polymers, fillers, plasticizers, catalysts, reactive diluents, anti-oxidants, ultraviolet light absorbers, flow control agents, and other formulating additives can be employed if desired.

Curable compositions of the invention can be applied as film forming coatings to a variety of substrates such as wood, metal, glass, cloth, plastic, foams and the like by a variety of application techniques such as air spraying, airless spraying, dipping, brushing and flow coating. The coating compositions are useful as basecoats or clearcoats and are particularly desirable as topcoat compositions for automobiles and trucks either as original finishes or as refinish coatings. Also, the coating compositions can be applied as color plus clear in base-coat-clearcoat applications.

The following examples are illustrative of the invention and are not intended to be limiting.

EXAMPLE 1

Synthesis of Bis-Azetidinol Functional Material Based on Bis-4-(Aminocyclohexyl)Methane (PACAM ®-20 Diamine Commercially Available from Texaco Chemicals)

| Charge | Amount |
| --- | --- |
| PACAM-20 | 210.0 g |
| n-butanol | 710.0 g |
| Feed A: | |
| Epichlorohydrin | 185.0 g |
| Feed B: | |
| Sodium hydroxide | 80.0 g |
| Deionized water | 80.0 g |

Feed A was added under agitation over 30 minutes into a 5 liter flask containing the charge. The contents of the flask were then heated to 60° C., and held at that temperature until the acid value (the acid value is the number of milligrams of potassium hydroxide required to neutralize the free acid present in one gram of the material) reached the theoretical value. The product thus formed was cooled to room temperature, followed by the addition of Feed B. The temperature was kept below 30° C. during the addition of Feed B.

The final product was isolated in N-butanol by filtering off the sodium chloride salt and removing the water by azetropic distillation. The product had following physical properties: total solids=41.0%, acid value=0.5, molecular weight determined by gel permeation chromatography using a polystyrene standard (GPC)=321, epoxy equivalent weight=infinite, pH in water-butanol mixture=11.2. The formation of the product was also identified by $13_C$ and $1_H$ nuclear magnetic resonance (nmr) spectroscopy.

EXAMPLE 2

Synthesis of Bis-Azetidinol Based on Isophorone Diamine

This product was prepared in the same manner as the bis-azetidinol of Example 1 except that PACAM-20 was replaced by isophorene diamine on a molar basis. The product had the following physical properties: total solids=42.0%, acid value=1.0, molecular weight by GPC=454.5, epoxy equivalent weight=infinite, pH in butanol-water mixture=11.4.

EXAMPLE 3

Synthesis of Bis-Azetidinol Based on Polyoxypropylene Diamine (Jeffamine ® D-400 Which is Commercially Available from Texaco Chemicals)

| Charge | Amount |
| --- | --- |
| JEFFAMINE D-400 | 465.0 g |
| Acetonitrile | 930.0 g |
| Feed A: | |
| Epichlorohydrin | 185.0 g |
| Feed B: | |
| Toluene | 930.0 g |
| Feed C: | |
| Sodium hydroxide | 80.0 g |
| Deionized water | 80.0 g |

Feed A was added over 30 minutes at room temperature into the charge in a 5 liter flask. The contents of the flask were then heated slowly to 75° C. and held at this temperature until the acid value reached the theoretical value. Afterwards, solvents were removed by distillation, followed by addition of Feed B. The product was cooled to room temperature and Feed C was added. The sodium chloride salt, thus formed, was removed by filtration. The product was isolated in toluene by removing water by azeotropic distillation.

The final product had the following physical properties: total solids=70% in toluene, acid value=1.0, epoxy equivalent weight=infinite, weight average molecular weight by GPC=541.

EXAMPLE 4

Synthesis of Tri-Azetidinol Functional Material Based on Triamine Derived from Reaction Product of Propylene Oxide with a Triol. (Jeffamine ® T-403 Commercially Available from Texaco Chemicals)

This product was made in the same way as the bis-azetidinol based on JEFFAMINE ® D-400 except that JEFFAMINE ® D-400 was replaced by JEFFAMINE ® T-403 on molar basis.

EXAMPLE 5

Stability of Polyazetidinol Functional Materials at Room Temperature in a N-Butanol-Water Mixture Having pH Greater Than 11.0

| Polyazetidinol | Stability after 4 Days | Stability After 7 Days |
| --- | --- | --- |
| Example 1 | Viscosity Increased | Gelled |
| Example 2 | Viscosity Increased | Gelled |
| Example 3 | Viscosity Increased | Gelled |
| Example 4 | Gelled | |

EXAMPLE 6

This example presents data showing the stability of polyazetidinol materials at 120° F. (49° C.) after 1, 2 and 4 weeks (pH was adjusted to 10.1 by addition of acetic acid). Initial viscosity (before storage at 120° F. (49° C.)) is shown in parenthesis.

| Polyazetidinol | Stability After 1 Week | Stability After 2 Weeks | Stability After 4 Weeks |
| --- | --- | --- | --- |
| Example 1 | E (E) | G | J |
| Example 3 | less than A (less than A) | less than A | B-C |
| Example 4 | Gelled (E) | Gelled | Gelled |

All the viscosities were measured by Gardner viscosity test tubes at 76° F.

EXAMPLE 7

This example presents data showing the stability of polyazetidinol materials at 120° F. (49° C.) after 1, 2, and 4 weeks (pH was adjusted to 8.1 by addition of acetic acid). Initial viscosity is shown in parenthesis.

| Polyazetidinol | Stability After 1 Week | Stability After 2 Weeks | Stability After 4 Weeks |
| --- | --- | --- | --- |
| Example 1 | F (F) | F-G | H-I |
| Example 2 | U (U) | W | Z |
| Example 3 | less than A (less than A) | less than A | A |
| Example 4 | Gelled (E) | Gelled | Gelled |

EXAMPLE 8

This example presents data showing film forming properties of polyazetidinols after baking the films at 180° F. (82° C.).

Films of 2.0 mil thickness were drawn on glass panels and baked for 15 minutes at 180° F. (82° C.). The hardness of the films was determined by solvent resistance which was evaluated by wetting a piece of cloth with solvent and rubbing that solvent back and forth on the film until the film was removed. The results are presented as double rubs (DR) in the following table.

| Polyazetidinol | Toluene | N-Butanol | Water |
| --- | --- | --- | --- |
| Example 1 | greater than 100 DR | 25 DR | 80 DR |
| Example 2 | greater than 80 DR | 15 DR | 80 DR |
| Example 4 | greater than 25 DR | 5 DR | 20 DR |

All these films were non-yellowing and transparent.

EXAMPLE 9

This example presents data showing film forming properties of polyazetidinols after baking the films at 230° F. (110° C.) for 1 hour. The hardness of the films was evaluated in the same way as in Example 8. Results are shown in the following table:

| Polyazetidinol | Toluene | N-Butanol | Water |
| --- | --- | --- | --- |
| Example 1 | greater than 125 DR | greater than 100 DR | greater than 120 DR |
| Example 2 | greater than | greater than | greater than |
| Example 4 | 120 DR greater than 75 DR | 100 DR greater than 40 DR | 120 DR greater than 60 DR |

Examples 8 and 9 show that the polyazetidinols of the present invention self-crosslink rapidly at elevated temperature forming films which are hard, non-yellowing and transparent.

EXAMPLE 10

This example shows the synthesis of a polyazetidinol functional acrylic polymer:

| Charge | Amount |
| --- | --- |
| n-butanol | 200.0 g |
| Feed A: | |
| Butyl acrylate | 303.0 g |
| Styrene | 203.0 g |
| Methyl methacrylate | 400.0 g |
| Acrylic acid | 100.0 g |
| Feed B: | |
| Tertiary butyl peracetate | 28.7 g |
| n-butanol | 92.7 g |
| Feed C: | |
| Dimethyl ethanol amine | 123.6 g |
| Feed D: | |
| Deionized water | 1400.0 g |
| Feed E: | |
| PACAM based bis-azetidinol of Example 1 (37.0% solid in n-butanol) | 298.4 g |

Charge was heated to reflux (about 117° C.) under nitrogen atmosphere. Feed A was added over 3 hours and Feed B was added over 3.5 hours. Upon the completion of Feed B, the contents of the flask were cooled below 100° C. Feed C and Feed D were added at 90° C. and 80° C., respectively. Feed E was added after cooling the polymer to room temperature.

The final product had the following physical properties: total solids=36.0% in water-n-butanol mixture, pH=9.02, viscosity=37,000 centipoise, number average molecular weight by GPC=13,494, weight average molecular weight by GPC=36,124, the average particle size=133 nanometer.

EXAMPLE 11

This example presents data showing the film forming properties of the polyazetidinol functional acrylic polymer prepared in Example 10:

The resin described in Example 10 was reduced to 25 percent solids with deionized water and then applied (using a 15-mil, number 24 wet film applicator from Paul N. Gardner Company, Inc) to four steel panels electrocoated with UNI-PRIME® primer, commercially available from PPG Industries, Inc. The coated panels were baked at 200° F. (93° C.), 250° F. (121° C.), 275° F. (135° C.) and 300° F. (149° C.) for 30 minutes.

After baking, dry film thickness ranged from 1.8 to 2.0 mils and all of the films were glossy and transparent. The films were evaluated as follows:

Gloss ranged from 80 to 90 degrees measured with a 20 degree angle Hunter Lab Glossmeter from Hunter Associates Laboratory, Inc.

Distinctness of Image was between 60 and 75 as measured with a Glow-Box, model GB-11, commercially available from I²R in Cheltenham, Pa.

The films demonstrated solvent resistance to 100 double rubs of methyl ethyl ketone, xylene and N-methyl-2-pyrolidone. Additionally, all the films exhibited H to 3H pencil hardness.

Films baked at 200° F. (93° C.) and 250° F. (121° C.) showed no yellowing, however, films baked at 270° F. (135° C.) and 300° F. (149° C.) showed some yellowing.

What is claimed is:

1. A reaction product of a polycarboxylic acid group containing polymeric material and a polyazetidinol represented by the following structural formula:

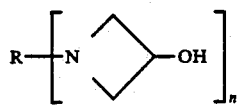

wherein R is alkylene, arylene, aralkylene, cycloalkylene or a heteroatom substituted derivative thereof, and n is an integer of from 2 to 4.

2. The reaction product of claim 1 wherein R is derived from bis-4-(aminocyclohexyl)methane.

3. The reaction product of claim 1 wherein R is derived from isophorone diamine.

4. The reaction product of claim 1 wherein R is derived from polyoxypropylene diamine.

5. The reaction product of claim 1 wherein R is derived from a triamine derived from the reaction product of propylene oxide with a triol.

6. The reaction product of claim 1 which is an ungelled reaction product.

7. The reaction product of claim 1 which is a cured reaction product.

8. The reaction product of claim 1 wherein the polycarboxylic group containing polymer is an acrylic polymer.

9. A curable composition comprising a base neutralized acid functional water dispersible polymer and a polyazetidinol represented by the following structural formula:

wherein R is alkylene, arylene, aralkylene, cycloalkylene or a heteroatom substituted derivative thereof and n is an integer of from 2 to 4.

10. A curable composition comprising a base neutralized acid functional water soluble polymer and a polyazetidinol represented by the following structural formula:

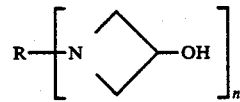

wherein R is alkylene, arylene, aralkylene, cycloalkylene or a heteroatom substituted derivative thereof and n is an integer of from 2 to 4.

11. An aqueous coating composition comprising a waterborne film forming vehicle, an aminoplast crosslinking agent and an additive amount of a polyazetidinol represented by the following structural formula:

wherein R is alkylene, arylene, aralkylene, cycloalkylene or a heteroatom substituted derivative thereof and n is an integer of from 2 to 4.

12. The aqueous coating composition of claim 11 wherein R is derived from bis-4-(aminocyclohexyl)methane.

13. The aqueous coating composition of claim 11 wherein R is derived from isophorone diamine.

14. The aqueous coating composition of claim 11 wherein R is derived from polyoxypropylene diamine.

15. The aqueous coating composition of claim 11 wherein R is derived from a triamine derived from the reaction product of propylene oxide with a triol.

* * * * *